United States Patent [19]
Miki et al.

[11] Patent Number: 5,814,472
[45] Date of Patent: Sep. 29, 1998

[54] MEASUREMENT OF LDL-CHOLESTEROL

[75] Inventors: Yutaka Miki; Nobuko Imajo; Isao Koyama; Toshiro Hanada, all of Amagasaki, Japan

[73] Assignee: Wako Pure Chemical Industries, Ltd., Osaka, Japan

[21] Appl. No.: 943,008

[22] Filed: Oct. 2, 1997

[30] Foreign Application Priority Data

May 13, 1997 [JP] Japan ................................. 9-137713
May 13, 1997 [JP] Japan ................................. 9-137714

[51] Int. Cl.[6] .............................. C12Q 1/60; C12Q 1/32; C12Q 1/00; C12Q 1/44
[52] U.S. Cl. ................................ 435/11; 435/26; 435/25; 435/4; 435/19; 435/28; 536/46; 536/103; 536/1.11
[58] Field of Search .............................. 435/11, 26, 25, 435/4, 19, 28; 536/46, 103, 1.11

[56] References Cited

U.S. PATENT DOCUMENTS

| | | | |
|---|---|---|---|
| 4,544,630 | 10/1985 | Ziegenhorn et al. | 435/11 |
| 5,286,626 | 2/1994 | Law et al. | 435/11 |
| 5,320,968 | 6/1994 | Seman | 435/11 |
| 5,384,248 | 1/1995 | Sakata et al. | 435/11 |
| 5,411,870 | 5/1995 | Law et al. | 435/11 |

FOREIGN PATENT DOCUMENTS

| | | |
|---|---|---|
| 0 676642 A1 | 4/1995 | European Pat. Off. . |
| A-58-165800 | 9/1983 | Japan . |
| A 6-242110 | 9/1994 | Japan . |
| A-7-280812 | 10/1995 | Japan . |
| WO 96/28734 | 9/1996 | Japan . |
| B2 2 609 505 | 2/1997 | Japan . |
| A 9-211002 | 8/1997 | Japan . |
| 9629599 | 9/1996 | WIPO . |

OTHER PUBLICATIONS

Sherma et al, Clin. Chem., vol. 36(3), pp. 529–532, 1990.

*Primary Examiner*—Louise N. Leary
*Attorney, Agent, or Firm*—Armstrong, Westerman, Hattori, McLeland & Naughton

[57] ABSTRACT

Cholesterol in low density lipoproteins can be measured specifically and precisely by optically measuring a reaction product of a living sample with cholesterol oxidase or cholesterol dehydrogenase in the presence of an amphoteric surfactant. In addition to the above processes for measurement, the present invention provides reagent compositions and kits for measuring cholesterol in low density lipoprotein.

34 Claims, No Drawings

MEASUREMENT OF LDL-CHOLESTEROL

BACKGROUND OF THE INVENTION

This invention relates to a process for measuring cholesterol in low density lipoproteins (hereinafter referred to as "LDL") present in living body samples such as serum, plasma, etc.

Major components of lipids in serum are cholesterol, triglycerides, phospholipids, etc. These serum lipids bind to apoproteins to form lipoproteins which circulate in the blood. The lipoproteins can be classified by differences in density into high density lipoproteins (HDL), low density lipoproteins (LDL), very low density lipoproteins (VLDL), and chylomicrons (CM), etc. Among these lipoproteins, HDL has a function of carrying excess cholesterol deposited on tissues to a liver, and has an anti-asteriosclerotic action. On the other hand, LDL is a major carrier of cholesterol from a liver to each tissue. An increase of LDL seems to have an intimate relation to generation of arteriosclerosis.

Therefore, the cholesterol in LDL (hereinafter referred to as "LDL-cholesterol) is regarded as a risk factor for arteriosclerosis, and ischemic heart disease (coronary arteriosclerotic disease). Thus, the content of LDL-cholesterol is an important indication of diagnosis, therapy and prophylaxis of these diseases.

As methods for measuring LDL-cholesterol, there have been known a precipitation method, an ultracentrifugal method, an electrophoresis method, and a Friedewald method. Among these methods, the precipitation method, the ultracentrifugal method and the electrophoresis method have complicated procedures due to pretreatment steps such as separation of LDL from unnecessary lipoproteins other than LDL by precipitation/ultracentrifugation treatments, ultracentrifugation treatment or electrophoresis treatment. Thus, these methods has a problem in that direct measurement using only an autoanalyzer which is widely used in the field of clinical tests is impossible.

On the other hand, according to the Friedewald method known by the Friedewald equation, wherein a total cholesterol value, a HDL-cholesterol value and a triglyceride value are used for computation, it has a problem in that it is impossible to measure an accurate LDL-cholesterol amount in the case of using a sample containing 500 mg/dl or more of triglycerides.

In order to solve the above-mentioned problems, various methods have been developed. For example, JP-A 7-280812 discloses a method comprising coagulating LDL using a coagulant and/or an antibody, eliminating (consuming) cholesterol contained in lipoproteins other than LDL by introducing it into another reaction system not pertaining to the quantitative reaction, dissolving the coagulated LDL to a degree of capable of conducting the quantitative reaction using a surfactant and/or an inorganic salt, and measuring the absorbance of the solution by subjecting the LDL-cholesterol to the quantitative reaction.

But since this method employs a three-reagent system or a four-reagent system at the measurement, it can only be applied to a few autoanalyzers which can be possible to use such multi-reagent systems. Many autoanalyzers usually used for clinical tests cannot be used, since these autoanalyzers can be used for only a two-reagent method. Further, this method also has a problem in that since a number of reagents are used, reproducibility of measured values is lowered.

In order to measure LDL-cholesterol without complicated pre-treatments, there is a process disclosed in JP-A 58-165800. But according this process, since the usable concentrations of a surfactant, and cholesterol esterase, for example, in reagents are limited, the preparation of reagents becomes complicated. Further, measuring conditions such as the pH at the time of measurement, intervals of measuring times, etc. should be set severely. Moreover, since the cholesterol in HDL reacts to some extent, the LDL-cholesterol can only be measured by a kinetic measurement, i.e. a rate assay. Thus, such a process cannot be said as a practical measuring process.

On the other hand, WO 96/29599 discloses a process for measuring cholesterol in LDL or VLDL, in the presence of a sugar compound and/or a nonionic or anionic surfactant, but said process is insufficient in precision.

SUMMARY OF THE INVENTION

It is an object of the present invention to provide a process for measuring LDL-cholesterol in a living body sample directly using an autoanalyzer, or the like, without complicated pre-treatments for separating LDL from unnecessary lipoproteins other than LDL necessitated in known processes as mentioned above, and reagents used for such a process.

The present invention provides a process for measuring cholesterol in low density lipoproteins present in a living sample by optically measuring a reaction product of the living sample with a reagent, which comprises conducting the reaction of the living sample with cholesterol oxidase or cholesterol dehydrogenase in the presence of an amphoteric surfactant and at least one member selected from the group consisting of cyclodextrin and derivatives thereof.

The present invention also provides a process for measuring cholesterol in low density lipoproteins present in a living sample, which comprises
treating the living sample with a first reagent comprising at least one member selected from the group consisting of cyclodextrin and derivatives thereof,
measuring absorbance or transmittance of the resulting solution,
treating the resulting solution with a second reagent solution containing cholesterol oxidase,
measuring another absorbance or transmittance of the resulting final solution, and
providing the cholesterol amount in the living sample on the basis of the absorbance or transmittance data measured above,
wherein a coupler, a developer, peroxidase, an amphoteric surfactant and cholesterol esterase is contained in at least either the first reagent or the second reagent.

The present invention further provides a process for measuring cholesterol in low density lipoproteins present in a living sample using cholesterol dehydrogenase in place of the cholesterol oxidase.

The present invention still further provides a process for measuring cholesterol in a living sample, which comprises
reacting the living sample with cholesterol oxidase or cholesterol dehydrogenase in the presence of at least one compound selected from the group consisting of dimethyl-α-cyclodextrin and poly-β-cyclodextrin, and
measuring the cholesterol amount optically.

The present invention further provides reagents used for the processes mentioned above.

DESCRIPTION OF THE PREFERRED EMBODIMENTS

In order to measure the amount of cholesterol in low density lipoproteins in a living sample such as serum and plasma without a pre-treatment for separating LDL-cholesterol from unnecessary lipoproteins other than LDL, the present inventors have found that when LDL-cholesterol in the living sample was measured in the presence of an amphoteric surfactant and cyclodextrin and/or a derivative thereof, or in the presence of at least one compound selected from the group consisting of dimethyl-α-cyclodextrin, and poly-β-cyclodextrin, the cholesterol amount in LDL was obtained precisely and directly using an autoanalyzer without known complicated pre-treatments, and accomplished the present invention.

In accordance with the present invention, LDL-cholesterol in a living sample can be measured precisely in the presence of an amphoteric surfactant and cyclodextrin and/or a derivative thereof using, for example, an autoanalyzer.

One process for measuring LDL-cholesterol amount in a living sample of the present invention comprises conducting the reaction of the living sample with cholesterol oxidase or cholesterol dehydrogenase in the presence of an amphoteric surfactant and at least one member selected from the group consisting of cyclodextrin and derivatives thereof, and measuring the cholesterol amount optically, e.g. measuring optical changes in a conventional manner.

Another process for measuring LDL-cholesterol amount in a living sample of the present invention comprises treating the living sample with a first reagent comprising at least one member selected from the group consisting of cyclodextrin and derivatives thereof, measuring an optical change such as an absorbance or transmittance of the resulting solution, treating the resulting solution with a second reagent solution containing cholesterol oxidase (hereinafter referred to as "COD"), measuring another optical change such as an absorbance or transmittance of the resulting final solution, and providing the cholesterol amount in the living sample on the basis of the data of optical changes measured above, wherein a coupler, a developer, peroxidase, an amphoteric surfactant and cholesterol esterase are contained in at least either the first reagent or the second reagent.

A further process for measuring LDL-cholesterol amount in a living sample of the present invention comprises treating the living sample with a first reagent comprising at least one member selected from the group consisting of cyclodextrin and derivatives thereof, measuring an optical change such as absorbance, transmittance, etc. of the resulting solution, treating the resulting solution with a second reagent solution containing cholesterol dehydrogenase (hereinafter referred to as "CHD"), measuring another optical change such absorbance, transmittance, etc. of the resulting final solution, and providing the cholesterol amount in the living sample on the basis of the data of optical changes measured above, wherein nicotinamide adenine dinucleotide (phosphate), an amphoteric surfactant and cholesterol esterase are contained in at least either the first reagent or the second reagent.

A reagent composition for measuring LDL-cholesterol of the present invention comprises cholesterol oxidase or cholesterol dehydrogenase, an amphoteric surfactant and cyclodextrin and/or a derivative thereof.

A further reagent composition for measuring LDL-cholesterol of the present invention comprises (a) a first reagent containing cyclodextrin and/or a derivative thereof, (b) a second reagent containing COD, and (c) a coupler, a developer, peroxidase (hereinafter referred to as "POD"), an amphoteric surfactant and cholesterol esterase (hereinafter referred to as "CHE") being contained in at least either the first reagent or the second reagent.

A still further reagent composition for measuring LDL-cholesterol of the present invention comprises (a) a first reagent containing cyclodextrin and/or a derivative thereof, an amphoteric surfactant and CHE, (b) a second reagent containing COD and CHE, and (c) a coupler, a developer and POD being contained in at least either the first reagent or the second reagent.

The reagents of the present invention can be used in the form of a kit comprising a first container containing a first reagent comprising cyclodextrin and/or a derivative thereof, an amphoteric surfactant, CHE and a coupler (or a developer); and a second container containing a second reagent comprising COD, CHE, POD and a developer (or a coupler).

When at least one compound selected from the group consisting of dimethyl-α-cyclodextrin, and poly-β-cyclodextrin is used as the derivative of cyclodextrin, the use of an amphoteric surfactant can be omitted.

In such a case, the process of the present invention concretely comprises reacting the living sample with cholesterol oxidase or cholesterol dehydrogenase in the presence of at least one compound selected from the group consisting of dimethyl-α-cyclodextrin and poly-β-cyclodextrin, and measuring the cholesterol amount optically, e.g. measuring optical changes in a conventional manner.

Another process for measuring LDL-cholesterol amount in a living sample of the present invention comprises treating the living sample with a first reagent comprising at least one member selected from the group consisting of dimethyl-α-cyclodextrin, and poly-β-cyclodextrin, measuring an optical change such as absorbance or transmittance of the resulting solution, treating the resulting solution with a second reagent solution containing cholesterol oxidase, measuring another optical change such as an absorbance or transmittance of the resulting final solution, and providing the cholesterol amount in the living sample on the basis of the data of optical changes measured above, wherein a coupler, a developer, peroxidase and cholesterol esterase are contained in at least either the first reagent or the second reagent.

A further process for measuring LDL-cholesterol amount in a living sample of the present invention comprises treating the living sample with a first reagent comprising at least one member selected from the group consisting of dimethyl-α-cyclodextrin and poly-β-cyclodextrin measuring an optical change such as absorbance, transmittance, etc. of the resulting solution, treating the resulting solution with a second reagent solution containing cholesterol dehydrogenase, measuring another optical change such as absorbance, transmittance, etc. of the resulting final solution, and providing the cholesterol amount in the living sample on the basis of the data of optical changes measured above wherein nicotinamide adenise dinucleotide (phosphate), and cholesterol esterase are contained in at least either the first reagent or the second reagent.

The reagent of the present invention comprises cholesterol oxidase or cholesterol dehydrogenase, and at least one compound selected from the group consisting of dimethyl-α-cyclodextrin, and poly-β-cyclodextrin.

A further reagent composition of the present invention comprises (a) a first reagent containing at least one compound selected from the group consisting of dimethyl-α-cyclodextrin, and poly-β-cyclodextrin, (b) a second reagent containing COD, and (c) a coupler, a developer, POD and CHE being contained in at least either the first reagent or the second reagent.

A still further reagent composition of the present invention comprises (a) a first reagent containing at least one compound selected from the group consisting of dimethyl-α-cyclodextrin, and poly-β-cyclodextrin, and CHE, (b) a second reagent containing COD, and (c) a coupler, a developer and POD being contained in at least either the first reagent or the second reagent.

These reagents of the present invention can be used in the form of a kit comprising a first container containing a first reagent comprising at least one compound selected from the group consisting of dimethyl-α-cyclodextrin and poly-β-cyclodextrin, CHE and a coupler (or a developer), and a second container containing a second reagent comprising COD, CHE, POD and a coupler (or a developer).

As the amphoteric surfactant, there can be use any ones so long as they can prevent cholesterol contained in lipoproteins other than LDL from pertaining to the cholesterol measuring reaction in the co-presence of cyclodextrin and/or a derivative thereof. Examples of the amphoteric surfactant are betaine derivatives, for example, alkylbetaines such as lauryl betaine, stearyl betaine, lauryldimethylammonium betaine, coconut betaine, coconut oil fatty acid amidopropyl betaine, and lauric acid amidopropyl betaine; imidazolinium betaine derivatives such as lauryl carboxymethyl hydroxyethyl imidazolinium betaine, 2-alkyl-N-carboxymethyl-N-hydroxyethyl imidazolinium betaines, 2-alkyl-N-carboxyethyl-N-hydroxyethyl imidazolinium betaine, and 2-undecyl-N-carboxymethyl-N-hydroxyethyl imidazolinium betaine; sulfobetaine derivatives such as N-octyl-N,N-dimethyl-3-ammonio-1-propanesulfonic acid, N-decyl-N,N-dimethyl-3-ammonio-1-propanesulfonic acid, N-dodecyl-N,N-dimethyl-3-ammonio-1-propanesulfonic acid, N-tetradecyl-N,N-dimethyl-3-ammonio-1-propanesulfonic acid, and N-hexadecyl-N,N-dimethyl-3-ammonio-1-propane-sulfonic acid; aminocarboxylic acid derivatives such as alkylglycines, alkyldi(aminoethyl) glycines, dioctyl-polyaminoethyl glycine, N-alkylpolyamino-ethyl glycines and β-alanine derivatives; imidazoline derivatives such as bis(2-undecyl-N-hydroxyethylimidazoline) chloroacetic acid complex and alkylimidazoline derivatives; amine oxide derivatives such as lauryldimethylamine oxide. These amphoteric surfactants can be used alone or as a mixture thereof. These amphoteric surfactants can be those commercially available, and those synthesized by conventional methods.

The using concentration of these amphoteric surfactants in the case of co-presence of cyclodextrin is not particularly limited so long as the amphoteric surfactant can prevent cholesterol contained in lipo-proteins other than LDL from pertaining to cholesterol measuring reaction. Preferable concentration of the amphoteric surfactant in the final (reaction) solution at the time of measuring cholesterol is 0.0001–10% (w/v), more preferably 0.001–1% (w/v).

The concentration of the amphoteric surfactant in each reagent when conducting a two-reagent method for measuring LDL-cholesterol changes depending on the amounts of the sample, the first reagent and the second reagent. When the amphoteric surfactant is contained only in the first reagent, the concentration of amphoteric surfactant is preferably selected from the range of 0.0002 to 20% (w/v), more preferably 0.002 to 2% (w/v). When the amphoteric surfactant is contained only in the second reagent, the concentration of amphoteric surfactant is preferably selected from the range of 0.0002 to 20% (w/v), more preferably 0.002 to 2% (w/v). Further when the amphoteric surfactant is contained both in the first and second reagents, the concentration of amphoteric surfactant is preferably 0.0001 to 20% (w/v), more preferably 0.001 to 2% (w/v) in the first reagent, and preferably 0.0001 to 20% (w/v), more preferably 0.001 to 20% (w/v) in the second reagent.

As the cyclodextrin and/or a derivative thereof, there can be used any ones so long as they can prevent the cholesterol contained in lipoproteins other than LDL from pertaining to the cholesterol measuring reaction in the co-presence of amphoteric surfactant.

Examples of cyclodextrin are α-cyclodextrin, β-cyclodextrin, γ-cyclodextrin, etc.

Examples of cyclodextrin derivatives are alkylated cyclodextrins such as 2,6-di-O-methyl-α-cyclodextrin, 2,3,6-tri-O-methyl-α-cyclodextrin, 2,6-di-O-ethyl-α-cyclodextrin, 2,3,6-tri-O-ethyl-α-cyclodextrin, 2,6-di-O-methyl-β-cyclodextrin, 2,3,6-tri-O-methyl-β-cyclodextrin, 2,6-di-O-ethyl-β-cyclodextrin, 2,3,6-tri-O-ethyl-β-cyclodextrin, 2,6-di-O-methyl-γ-cyclodextrin, 2,3,6-tri-O-methyl-γ-cyclodextrin, 2,6-di-O-ethyl-γ-cyclodextrin and 2,3,6-tri-O-ethyl-γ-cyclodextrin; hydroxyalkyl cyclodextrins such as 2-hydroxyethyl-α-cyclodextrin, 2-hydroxypropyl-α-cyclodextrin, 3-hydroxypropyl-α-cyclodextrin, 2,3-dihydroxypropyl-α-cyclodextrin, 2-hydroxyethyl-β-cyclodextrin, 2-hydroxypropyl-β-cyclodextrin, 3-hydroxypropyl-β-cyclodextrin, 2,3-dihydroxypropyl-β-cyclodextrin, 2-hydroxyethyl-γ-cyclodextrin, 2-hydroxypropyl-γ-cyclodextrin, 3-hydroxypropyl-γ-cyclodextrin and 2,3-dihydroxypropyl-γ-cyclodextrin; acylated cyclodextrins 2,3,6-tri-O-acetyl-α-cyclodextrin, 2,3,6-tri-O-acetyl-β-cyclodextrin and 2,3,6-tri-O-acetyl-γ-cyclodextrin; sugar-modified cyclodextrins such as 6-O-α-D-glucosyl-α-cyclodextrin, 6-O-α-maltosyl-α-cyclodextrin, 6-O-α-D-glucosyl-β-cyclodextrin, 6-O-α-maltosyl-β-cyclodextrin, 6-O-α-D-glucosyl-γ-cyclodextrin and 6-O-α-maltosyl-γ-cyclodextrin; carboxyalkylated cyclodextrins such as O-carboxymethyl-α-cyclodextrin, O-carboxymethyl-β-cyclodextrin and O-carboxymethyl-γ-cyclodextrin; polymer cyclodextrins such as poly-α-cyclodextrin, poly-β-cyclodextrin and poly-γ-cyclodextrin. As these cyclodextrins and derivative thereof, those commercially available can be used. Further, those synthesized by known methods disclosed in U.S. Pat. No. 3,453,258, U.S. Pat. No. 3,453,259, Polymer Journal, vol. 13, No. 8, pp. 777–781 (1981), JP-A 61-266401, JP-A 63-122701, and JP-A 62-243602, contents of all of which are hereby incorporated by reference, can also be used in the present invention.

The using concentration of these cyclodextrins and/or derivatives thereof is not particularly limited so long as these cyclodextrins and derivatives thereof can prevent contained in lipoproteins other than LDL from pertaining to cholesterol measuring reaction. Preferable concentration of the cyclodextrins and derivatives thereof in the final (reaction) solution at the time of measuring cholesterol is preferably 0.0001 to 10% (w/v), more preferably 0.001 to 1% (w/v).

Further, the concentration of the cyclodextrins and derivatives thereof in the first reagent when conducting a two-reagent method for measuring LDL-cholesterol changes depending on the amounts of the sample, the first reagent and the second reagent. Usually, the concentration is in the range of 0.0002 to 20% (w/v), preferably 0.002 to 2% (w/v).

These cyclodextrins and derivatives thereof can be used alone or as a mixture thereof.

According to the measuring processes of the present invention, conventional reagents used for measuring cholesterol can be used in addition to the above-mentioned amphoteric surfactants and cyclodextrins and derivatives thereof.

That is, LDL-cholesterol in a living sample such as serum, plasma, etc. can be measured specifically by a conventional method in the presence of cyclodextrin and/or a derivative thereof, for example, by using an enzymatic reaction.

Such a conventional process (oxidative color producing process) comprises decomposing the cholesterol ester in a sample with CHE to give free cholesterol and the fatty acid, oxidizing the product together with free cholesterol present from the beginning with COD to give cholest-4-en-3-on and hydrogen peroxide; conducting an oxidative color producing reaction of an oxidizable color producing reagent with the produced hydrogen peroxide in the presence of POD; and subjecting the produced oxidized dye to colorimetric determination.

Another conventional process (ultraviolet measuring process) comprises decomposing cholesterol ester in a sample with CHE to give free cholesterol and the fatty acid, reacting with nicotinamide adenine dinucleotide or its phosphate (hereinafter referred to as "NAD(P)") in the presence of the free cholesterol present from the beginning and CHD, and measuring the produced NAD(P)H using ultraviolet light of 340 nm.

COD used in the present invention is not particularly limited to its sources. There can be used those used conventionally in this field, for example, those derived from microorganisms such as Nocardia Genera and Pseudomonas Genera, and animal organs such as bovine pancreas. The using amount of COD in the final reaction solution at the time of measuring cholesterol is preferably 0.02 to 10 u/ml, more preferably 0.1 to 2 u/ml.

CHE used in the present invention is not particularly limited to its sources. There can be used those used conventionally in this field, for example, those derived from microorganisms such as Candida Genera and Pseudomonas Genera, and animal organs such as bovine pancreas. T using amount of CHE in the final reaction solution at the time of measuring cholesterol is preferably 0.02 to 10 u/ml, more preferably 0.1 to 2 u/ml.

POD used in the present invention is not particularly limited to its sources. There can be used those used conventionally in this field, for example, those derived from plants such as horseradish and radish; microorganisms such as molds and yeasts; and leukocytes and thyroids of animals. The using amount of POD in the final reaction solution at the time of measuring cholesterol is preferably 0.01 to 50 u/ml, more preferably 0.1 to 5 u/ml.

As the oxidizable color producing reagents used in the present invention, there can be used those which can produce a color when reacted with hydrogen peroxide in the presence of POD. Examples thereof are a combination of a coupler such as 4-aminoantipyrine (4-AA) and a developer which can produce a dye by oxidative condensation with the coupler, for example, a combination of 4-AA and a phenolic compound, a naphthol compound or an aniline compound, a combination of 3-methyl-2-benzothiazolinone hydrozone and an aniline compound, etc.; color producing agents which can produce a color by itself by oxidation such as 2,2'-azinobis(3-ethylbenzothiazolin-6-sulfonic acid), triphenylmethane leuco dyes, diphenylamine derivatives, benzidine derivatives, triallylimidazole derivatives, leuco methylane blue derivatives and o-phenylenediamine derivatives.

As the developer, there can be used phenyl compounds such as phenol, p-chlorophenol and 2,4-dichlorophenol; naphthanol compounds such as 1-naphthol, 1-naphtol-2-sulfonic acid, and 1-naphthol-2-carboxylic acid; aniline compounds such as N,N-diethylaniline, N-ethyl-N-(β-hydroxyethyl)-m-toluidine, N-ethyl-N-(2-hydroxy-3-sulfopropyl)-3,5-dimethoxyaniline, (DAOS), N-ethyl-N-(2-hydroxy-3-sulfopropyl)-3,5-dimethoxy-4-fluoroaniline (FDAOS), N-(2-hydroxy-3-sulfopropyl)-3,5-dimethoxyaniline (HDAOS), N-ethyl-N-(2-hydroxy-3-sulfopropyl)-m-toluidine (TOOS) and N-ethyl-N-(3-methylphenyl)-N'-succinyl-ethylenediamine (EMSE).

The using amount of the coupler, when the coupler is used in combination with a developer, changes depending on the kind of coupler, the kind of developer to be combined with. The concentration of the coupler in the final (reaction) solution at the time of measuring cholesterol is preferably 0.01 to 100 mM, more preferably 0.1 to 10 mM. When 4-AA is used as the coupler, the concentration of 4-AA in the final reaction solution at the time of measuring cholesterol is preferably 0.01 to 50 mM, more preferably 0.1 to 5 mM.

The using amount of developer changes depending on the kind of developer and the kind of coupler to be combined with. The concentration of the developer in the final reaction solution at the time of measuring cholesterol is preferably 0.01 to 50 mM, more preferably 0.1 to 5 mM.

Examples of the triphenylmethane leuco dyes are leuco Malachite Green, bis(p-diethylaminophenyl)-2-sulfophenylmethane, bis(p-diethylaminophenyl)-3,4-disulfopropoxyphenylmethane.disodium salt, etc.

Examples of the diphenylamine derivatives are bis[4-di (2-butoxyethyl)amino-2-methylphenyl]amine, N,N-bis(4-diethylamino-2-methylphenyl)-N'-p-toluenesulfonyl urea, etc.

Examples of the leucomethylene blue derivatives are 10-(carboxymethylaminocarbonyl)-3,7-bis(dimethylamino) phenothiazine.sodium salt, 10-[3-(methoxycarbonylaminomethyl) phenylmethylaminocarbonyl]-3,7-bis(dimethylamino) phenothiazine, etc.

Examples of the benzidine derivatives are benzidine, o-toluidine, o-dianisidine, 3,3'-diaminobenzidine, 3,3',5,5'-tetraaminobenzidine, etc.

Examples of the triallylimidazole derivatives are 2-(4-carboxyphenyl)-3-N-methylcarbamoyl-4,5-bis(4-diethylaminophenyl) imidazole, 2-(3-methoxy-4-diethylaminophenyl)-3N-metylcarbomoyl-4,5-bis(2-methyl-4-diethylaminophenyl) imidazole, etc.

The using amount of these color producing agents is properly selected from conventionally used ranges in this field.

CHD used in the present invention is not limited to its sources. Conventionally used ones, for example, those derived from Nocardia Genera, etc. can be used. The using amount in the final reaction solution at the time of measuring cholesterol is preferably 0.1 to 100 u/ml, more preferably 1 to 50 u/ml.

NAD(P) used in the present invention is not particularly limited, and those conventionally used in this field can also be used. The using amount of NAD(P) in the final (reaction) solution at the time of measuring cholesterol is preferably 0.02 to 50 mM, more preferably 0.1 to 10 mM.

The reagents for measuring LDL-cholesterol used in the present invention are those conventionally used for measuring LDL-cholesterol in a sample derived from a living body such as serum, plasma, etc. except for using the amphoteric surfactant and cyclodextrin and/or a derivative thereof. The conventionally used reagents include COD, CHE, POD, oxidizable color producing reagents, etc. used in the oxidative color producing process; CHE, CHD, NAD(P), etc. used in the violet light measuring process. These reagents are used in concentrations suitable for measuring LDL-cholesterol.

The reagents for measuring LDL-cholesterol used in the present invention can be prepared for a one- reagent method, a two-reagent method, or a three-or more-reagent method. When the reagents are separated in two or more reagents, the following compositions are preferable considering specificity, measuring precision, etc.

In the case of the oxidative color producing process, the first reagent includes cyclodextrin and/or a derivative thereof, and the second reagent includes COD. Other reagents such as amphoteric surfactants, enzymes such as CHE and POD, couplers and developers can be included in at least either the first or second reagent.

In the case of the ultraviolet measuring process, the first reagent includes cyclodextrin and/or a derivative thereof, and the second reagent includes CHD, and other reagents such as NAD(P) can be included in at least either the first or second reagent.

When the process of the present invention is carried out by a two-reagent method, a sample is treated with a first reagent including cyclodextrin and/or a derivative thereof, for example, by mixing the sample with the first reagent, and the treated sample is reacted with a second reagent including COD or CHD in the presence of the cyclodextrin and/or a derivative thereof and the amphoteric surfactant. Such steps mentioned above are preferable from the viewpoint of specificity, measuring accuracy, etc.

In the case of the oxidative color producing process, the following combinations of reagents are preferably used:
(i) a First reagent including cyclodextrin and/or a derivative thereof and an amphoteric surfactant,
a second reagent including COD, and
a coupler, a developer, POD and CHE being included in at least either the first regent or the second reagent,
(ii) a first reagent including cyclodextrin and/or a derivative thereof and CHE,
a second reagent including COD, and
a coupler, a developer, POD and an amphoteric surfactant being included in at least either the first reagent or the second reagent, and
(iii) a first reagent including cyclodextrin and/or a derivative thereof, amphoteric surfactant and CHE,
a second reagent including COD, and
a coupler, a developer and POD being included in at least either the first reagent or the second reagent.

In the case of the ultraviolet light measuring process, the following combinations of reagents are preferably used;
(i') a first reagent including cyclodextrin and/or a derivative thereof and an amphoteric surfactant,
a second reagent including CHD, and
NAD(P) and CHE being included in at least the first reagent or the second reagent,
(ii') a first reagent including cyclodextrin and/or a derivative thereof and CHE,
a second reagent including CHD, and
NAD(P) and an amphoteric surfactant being included in at least the first reagent or the second reagent, and
(iii') a first reagent including cyclodextrin and/or a derivative thereof, an amphoteric surfactant and CHE,
a second reagent including CHD, and
NAD(P) being included in either the first reagent or the second reagent.

When the reagents for measuring LDL-cholesterol of the present invention is prepared for a two-reagent method, it is preferable to co-exist the amphoteric surfactant and/or CHE together with cyclodextrin and/or a derivative thereof in the first reagent in order to improve the specificity to the LDL-cholesterol and measuring accuracy of LDL-cholesterol.

Further, among the combinations of reagents mentioned above, when the amphoteric surfactant is co-existed with CHE, there is a possibility of lowering stability of CHE activity by the amphoteric surfactant. Thus, in this case, it is preferable to include CHE in both the first reagent and the second reagent. In the case of reagents for the oxidative color producing process, the first reagent includes cyclodextrin and/or a derivative thereof, an amphoteric surfactant and CHE, the second reagent includes COD and CHE, and a coupler, a developer and POD are included in at least either the first reagent or the second reagent. In the case of reagents for the ultraviolet measuring process, the first reagent includes cyclodextrin and/or a derivative thereof, an amphoteric surfactant, and CHE, the second reagent include CHD and CHE, and NAD(P) is included in at least either the first reagent or the second reagent.

In addition, in the above-mentioned combination of reagents for the oxidative color producing process, either one of a coupler and a developer is preferably included in the first reagent and the rest of them is preferably included in the second reagent.

The reagents for measuring LDL-cholesterol of the present invention may include one or more buffers. Buffers usable in the present invention change depending on the combinations of various enzymes and oxidative color producing reagents, but conventional buffers usually used in this field can be used. It is preferable to use buffers having a buffering action in the range of pH 5 to 11. The buffers can preferably used in a concentration of 1 mM to 5M, more preferably 5 mM to 1M.

Considering the specificity to LDL-cholesterol, preferable examples of the buffers are aminoethanesulfonic acid derivatives such as N-(2-acetamido)-2-aminoethanesulfonic acid (ACES), N,N-bis(2-hydroxyethyl)-2-aminoethanesulfonic acid (BES), N-cyclohexyl-2-aminoethanesulfonic acid (CHES), 2-[4-(2-hydroxyethyl)-1-piperazinyl]ethanesulfonic acid (HEPES), 2-morpholinoethanesulfonic acid (MES), piperazine-1,4-bis (2-ethanesulfonic acid) (PIPES) and N-tris(hydroxymethyl) methyl-2-aminoethanesulfonic acid (TES); aminopropanesulfonic acid derivatives such as N-cyclohexyl-3-aminopropanesulfonic acid (CAPS), N-cyclohexyl-2-hydroxy-3-aminopropanesulfonic acid (CAPSO), 3-[N,N-bis(2-hydroxyethyl)amino]-2-hydroxypropanesulfonic acid (DIPSO), 3-[4-(2-hydroxyethyl)-1-piperazinyl] propanesulfonic acid (EPPS), 2-hydroxy-3-[4-(2-hydroxyethyl)-1-piperazinyl]propanesulfonic acid (HEPPSO), 3-morpholinopropanesulfonic acid (MOPS), 2-hydroxy-3-morpholinopropanesulfonic acid (MOPSO), piperazine-1,4-bis(2-hydroxy-3-propanesulfonic acid) (POPSO), N-tris(hydroxymethyl)methyl-3-aminopropanesulfonic acid (TAPS) and 2-hydroxy-N-tris (hydroxymethyl)methyl-3-aminopropanesulfonic acid (TAPSO); aliphatic amines having a carboxyl group or a sulfonic acid group such as glycine derivatives, e.g. N-(2-acetamido)iminodiacetic acid (ADA), N,N-bis(2-hydroxyethyl)glycine (Bicine), N-[tris(hydroxymethyl) methyl]glycine (Tricine), etc.

The reagents for measuring LDL-cholesterol of the present invention may include one or more ionic compounds, for example, polyaniones such as dextran sulfate, heparin, heparan sulfate, and tungstophosphoric acid, singly or as a mixture thereof. Further, it is possible to use divalent cations such as $Mg^{2+}$, $Mn^{2+}$ and $Ca^{2+}$ (or one or more metal salts capable of producing these divalent cations) in combination with the ionic compound. The concentration of these additives is not particularly limited. The concentration of the ionic compound in the final (reaction) solution is preferably 0.01 to 10% (w/v). The concentration of the divalent cations in the final (reaction) solution is preferably 0.1 to 200 mM.

The reagents for measuring LDL-cholesterol of the present invention may include one or more polyclonal antibodies or monoclonal antibodies in order to prevent the cholesterol in lipoproteins other than LDL from pertaining to the cholesterol measuring reaction.

Examples of such antibodies are anti-apolipoprotein A antibody, anti-apolipoprotein C antibody, anti-apolipoprotein E antibody, anti-α-lipoprotein antibody, etc.

The concentration of these antibodies are not particularly limited so long as they can prevent the cholesterol contained in lipoproteins other than LDL from pertaining to the cholesterol measuring reaction. It is preferable to add these antibodies to the final (reaction) solution so as to make the concentration 0.001 to 10 mgAb/ml, more preferably 0.01 to 1 mgAb/ml.

The reagents for measuring LDL-cholesterol of the present invention may further contain one or more surfactants other than the amphoteric surfactants conventionally used in this field, for example, nonioic surfactants such as polyoxyethylene isooctylphenyl ethers, polyethylene alkylphenyl ethers, polyoxyethylene nonylphenyl ethers, polyoxyethylene cetyl ethers, polyoxyethylene oleyl ethers, polyethyl glycol monolaurate and polyethylene lauryl ether; cationic surfactants such as stearyl trimethylammonium chloride, and alkylbenzyldimethylammonium chlorides; anionic surfactants such as cholic acid, deoxycholic acid, and polyoxyethyelne alkylphenyl ether sodium sulfonate. These surfactants can be used singly or as a combination thereof. The concentration of these surfactants is not particularly limited, but preferably in the range of 0.0001 to 10% (w/v), more preferably 0.001 to 1% (w/v) in the final (reaction) solution.

The LDL-cholesterol can be measured by the present invention in the case of the two-reagent method as follows.
1) Oxidative color producing process A living sample such as serum and plasma is mixed with a first reagent containing, for example, an amphoteric surfactant, cyclodextrin and/or a derivative thereof, CHE and a coupler (or a developer), and if necessary one or more buffers, antibodies, ionic compounds, divalent cations, etc. to treat the sample, followed by reaction at 2° to 40° C. for 1 to 30 minutes and measurement of absorbance ($OD_1$). Then, the reaction solution is mixed with a second reagent containing, for example, COD, CHE, POD and a developer (or a coupler), and if necessary, one or more buffers, etc., followed by reaction at 2° to 40° C. for 1 to 60 minutes and measurement of absorbance ($OD_2$). Then, absorbance ($OD_3$) is obtained by subtracting the value derived from $OD_1$ (for example, a value obtained by multiplying $OD_1$ by a correction coefficient) from $OD_2$. The resulting $OD_3$ is applied to a calibration curve showing a relationship between the LDL-cholesterol concentrations and the $OD_3$ obtained by the same procedures as mentioned above using standard solutions, etc. containing known cholesterol amounts. Thus, the LDL-cholesterol value in the living sample can be obtained.
2) Ultraviolet measuring process A living sample such as serum and plasma is mixed with a first reagent containing, for example, an amphoteric surfactant, cyclodextrin and/or a derivative thereof and CHE, and if necessary, one or more buffers, antibodies, ionic compounds, divalent cations, etc. to treat the sample, followed by reaction at 2° to 40° C. for 1 to 30 minutes and measurement of absorption ($OD_1'$) at 340 nm. Then, the reaction solution is mixed with a second reagent containing, for example, CHD, CHE and NAD(P), and if necessary, one or more buffers, followed by reaction at 2° to 40° C. for 1 to 60 minutes and measurement of absorption ($OD_2'$) at 340 nm. Then, absorbance ($OD_3'$) is obtained by subtracting the value derived from $OD_1$ (for example, a value obtained by multiplying $OD_1'$ by a correction coefficient) from $OD_2'$. The resulting $OD_3'$ is applied to a calibration curve showing a relationship between the LDL-cholesterol concentrations and the $OD_3'$ obtained by the same procedures as mentioned above using standard solutions, etc. containing known cholesterol amounts. Thus, the LDL-cholesterol value in the living sample can be obtained.

When the LDL-cholesterol measuring process of the present invention is carried out by a one-reagent method, the following steps can be employed.
1) Oxidative color producing process A living sample such as serum and plasma is mixed with a reagent solution containing, for example, CHE, COD, POD, an oxidizable color producing reagent, an amphoteric surfactant and cyclodextrin and/or a derivative thereof, and if necessary, one or more buffers, antibodies, ionic compounds, divalent cations, etc., followed by reaction at 2° to 40° C. for 1 to 30 minutes and measurement of absorbance ($OD_S$). A blank value ($OD_{B1}$) is obtained by using the same reagents as mentioned above and conducting the same procedures as mentioned above, while using physiological saline in place of the living sample. Then, absorbance ($OD_R$) is obtained by subtracting $OD_{B1}$ from $OD_S$. The resulting $OD_R$ is applied to a calibration curve showing a relationship between the LDL-cholesterol concentrations and $OD_R$ obtained by using the same procedures as mentioned above using standard solutions, etc. containing known cholesterol amounts. Thus, the LDL-cholesterol value in the living body sample can be obtained.
2) Ultraviolet measuring process A living sample such as serum and plasma is mixed with a reagent solution containing, for example, CHE, CHD, NAD(P), an amphoteric surfactant, cyclodextrin and/or a derivative thereof, and if necessary, one or more buffers, antibodies, ionic compounds, divalent cations, etc., followed by reaction at 2° to 40°C. for 1 to 30 minutes and measurement of absorbance ($OD_S'$) at 340 nm. A blank value ($OD_{B1}'$) is obtained by using the same reagents as mentioned above and conducting the same procedures as mentioned above, while using physiological saline in place of the living sample. Then, absorbance ($OD_R'$) is obtained by subtracting $OD_{B1}'$ from $OD_S'$. The resulting $OD_S'$ is applied to a calibration curve showing a relationship between the LDL-cholesterol concentrations and $OD_S'$ obtained by using the same procedures as mentioned above using standard solutions, etc. containing known cholesterol amounts. Thus, the LDL-cholesterol value in the living sample can be obtained.

In the above cases, instead of the absorbance as an optical change, other optical changes such as transmittance can be used.

The kit for measuring the LDL-cholesterol of the present invention of the present invention is used for LDL-cholesterol in a sample derived from a living body such as serum and plasma, and has the following constitution:

1) For oxidative color producing process a first container containing a first regent comprising cyclodextrin and/or a derivative thereof, an amphoteric surfactant, CHE, and a coupler (or a developer, and a second container containing a second reagent comprising COD, CHE, POD and a developer (or a coupler).

2) For ultraviolet measuring process a first container containing a first reagent comprising cyclodextrin and/or a derivative thereof, an amphoteric surfactant, and CHE, and a second container containing a second reagent comprising CHD, NAD(P), and CHE.

Preferable embodiments and examples of individual constituting elements are as mentioned above. Needless to say, the kit may be combined with LDL-cholesterol standard substances.

The LDL-cholesterol measuring processes of the present invention can be conducted in the presence of an amphoteric surfactant and cyclodextrin and/or a derivative thereof, or in the presence of at least one compound selected from the group consisting of dimethyl-α-cyclodextrin, and poly-β-cyclodextrin, so that the cholesterol in lipoproteins other than LDL, e.g. not only HDL but also VLDL, CM, etc. does not substantially pertain to the reaction and LDL-cholesterol is specifically reacted, resulting in making LDL-cholesterol measurement by the end point assay, which was impossible by conventional processes, possible. Further, as to the standard substances, it is not necessary to use pure LDL-cholesterol. Instead, it is possible to use a standard solution containing cholesterol or a standard serum having the same properties such as viscosity and specific gravity as normal serum.

The present invention is illustrated by the following Examples, but not limited thereto.

EXAMPLE 1

Using Hitachi 7170 type autoanalyzer (mfd. by Hitachi, Ltd.), cholesterol in various lipoproteins fractionated by ultracentrifugation was measured according to a process of the present invention for studying reactivity of cholesterol.

[Samples]

As samples, there were used LDL fractions, HDL fractions, VLDL fractions and CM fractions obtained from serum by fraction using a known ultracentrifugation method.

Cholesterol in each sample was measured previously using a commercially available reagent kit for measuring total cholesterol (L-type Wako CHO.H, a trade name, mfd. by Wako Pure Chemical Industries, Ltd.) in accordance with a standard procedure described in the manual for the kit.

[Reagents]

(Reagent 1)

R-1: 50 mM piperazine-1,4-bis(2-ethanesulfonic acid) (PIPES)-NaOH buffer (pH 7.0) containing
    (i) 2,6-di-O-methyl-α-cyclodextrin (mfd. by Wako Pure Chemical Industries, Ltd., hereinafter referred to as "DM-α-CD") 0.06% (w/v);
    (ii) N-(2-hydroxy-3-sulfopropyl)-3,5-dimethoxyaniline Na salt (HDAOS, mfd. by Dojindo Laboratories Co., Ltd.) 0.6 mM; and
    (iii) $Na_2SO_4$ 0.4M R-2: 50 mM PIPES-NaOH buffer (pH 7.0) containing
    (i) COD (mfd. by Amano Pharmaceutical Co., Ltd.) 4 u/ml;
    (ii) CHE (mfd. by Asahi Kasei Kogyo K.K.) 4 u/ml;
    (iii) POD (mfd. by Toyobo Co., Ltd.) 6 u/ml; 4-AA 3 mM; and
    (iv) an amphoteric surfactant shown in Table 1 0.01% (w/v).

(Amphoteric surfactants)

The following ones were used:

Lipomin LA (a trade name, mfd. by Lion Corp.), an aminocarboxylic acid derivative.

Softazoline LPB-R (a trade name, mfd. by Kawa-Ken Fine chemical Co., Ltd.), lauric acid amidopropyl betaine Softazoline CL (a trade name, mfd. by Kawa-Ken Fine Chemical Co., Ltd.), 2-alkyl-N-carboxymethyl-N-hydroxyethyl imidazolinium betaine Anhitol 24B (a trade name, mfd. by Kao Corp.), lauryl betaine Enadicol L-30AN (a trade name, mfd. by Lion Corp.), sodium N-lauroyl-N-methyl-β-alanine Zwittergent 3-08 (a trade name, mfd. by Wako Pure Chemical Industries, Ltd.), N-octyl-N,N-dimethyl-3-ammonio-1-propanesulfonic acid.

(Reagent 2)

R-1: The same as Reagent 1

R-2: The same as Reagent 1 except for using the following surfactants in place of the amphoteric surfactants.

(Surfactants)

Emalgen A-90 (a trade name, mfd. by Kao Corp.), polyoxyethylene derivative

Emalgen 709 (a trade name, mfd. by Kao Corp.), polyoxyethylene higher alcohol ether Triton X-100 (a trade name, mfd. by Rohm & Haas Co.) polyoxyethylene alkylphenyl ether (Reagent 3)

R-1: 50 mM PIPES-NaOH buffer (pH 7.0) containing HDAOS 0.6 mM and $Na_2SO_4$ 0.4M.

R-2: 50 mM PIPES-NaOH buffer (pH 7.0) containing
    (i) COD (mfd. by Amano Pharmaceutical Co., Ltd.) 4 u/ml;
    (ii) CHE (mfd. by Asahi Kasei Kogyo K.K.), 4 u/ml;
    (iii) POD (mfd. by Toyobo Co, Ltd.) 6 u/ml, and
    (iv) 4-AA 3 mM.

[Measuring conditions]

Measuring parameters were set as follows to measure cholesterol in each sample.

Measuring method; 2 Point end [16]–[34]

Sample amount: 3 μl

R-1: 270 μl

R-2: 90 μl

Measuring wavelength: 700/600 nm

Measuring temperature: 37° C.

Standard substance concentration: 100 mg/dl
[Results]

Conversion (%) of each lipoprotein was obtained by inserting the cholesterol value obtained from each sample and the cholesterol value in each sample using a commercially available kit into the following formula:

$$\text{Conversion (\%)} = \frac{\text{Cholesterol value obtained from a sample}}{\text{Cholesterol value obtained by using a commercially available kit}} \times 100$$

The results are shown, in Table 1.

TABLE 1

| | Surfactant | | Conversion of lipoproteins (%) | | | |
|---|---|---|---|---|---|---|
| | | | LDL | HDL | VLDL | CM |
| Reagent 1 | Lipomin LA | Amphoteric | 94 | 4 | 6 | 4 |
| | Softazoline LBP-R | " | 101 | 0 | 13 | 5 |
| | Softazoline CL | " | 100 | 0 | 0 | 2 |
| | Anhitol 24B | " | 98 | 0 | 8 | 3 |
| | Enadicol L-30AN | " | 98 | 0 | 11 | 7 |
| | Zwitter 3-08 | " | 100 | 1 | 9 | 6 |
| Reagent 2 | Emalgen A-90 | Nonionic | 65 | 54 | 51 | 20 |
| | Emalgen 709 | " | 86 | 45 | 24 | 25 |
| | Triton X-100 | " | 93 | 42 | 0 | 19 |
| Reagent 3 | No addition of surfactant No addition of DM-α-CD | | 103 | 86 | 99 | 98 |

As is clear from the results shown in Table 1, when Reagent 1 is used, since the cholesterol is measured in the presence of an amphoteric surfactant and DM-α-CD, lipoproteins other than LDL are hardly reacted, resulting in becoming possible to measure the cholesterol in LDL specifically. In contrast, when the measurement is carried out in the presence of a nonionic surfactant and DM-α-CD (Reagent 2) and in the absence of a surfactant and DM-α-CD (Reagent 3), lipoproteins other than LDL also react, resulting in failing to measure LDL-cholesterol specifically.

As mentioned above, in order to measure the cholesterol in LDL specifically, it is necessary to carry out the measurement in the presence of an amphoteric surfactant and cyclodextrin and/or a derivative thereof.

EXAMPLE 2

Another typical example of the kit for measuring LDL-cholesterol in a living sample is as follows.
(1) First reagent (pH 6–8)
  Cyclodextrin and/or a derivative thereof,
  Amphoteric surfactant,
  CHE, and
  Coupler (or a developer)
(2) Second reagent (pH 6–8)
  COD,
  CHE,
  POD, and
  Developer (or a coupler).

The same results as obtained in Example 1 were obtained using said kit.

EXAMPLE 3

Using Hitachi 7170 type autoanalyzer (mfd. by Hitachi, Ltd.), cholesterol in various lipoproteins fractionated by ultracentrifugation was measured according to a process of the present invention for studying reactivity of cholesterol.
[Samples]

As samples, there were used LDL fractions, HDL fractions, VLDL fractions and CM fractions obtained from serum by fraction using a known ultracentrifugation method.

Cholesterol in each sample was measured previously using a commercially available reagent kit for measuring total cholesterol (L-type Wako Cho.H, a trade name, mfd. by Wako Pure Chemical Industries, Ltd.) in accordance with a standard procedure described in the manual for the kit.
[Reagents]
  R-1: 100 mM PIPES-NaOH buffer (pH 7.0) containing
    (i) HDAOS 0.6 mM,
    (ii) $Na_2SO_4$ 0.4M, and
    (iii) a cyclodextrin derivative shown in Table 2
  R-2: 100 mM PIPES-NaOH buffer (pH 7.0) containing
    (i) COD (mfd. by Amano Pharmaceutical Co., Ltd.) 4 u/ml,
    (ii) CHE (mfd. by Asahi Kasei Kogyo K.K.) 4 u/ml,
    (iii) POD (mfd. by Toyobo Co., Ltd.) 6 u/ml, and
    (iv) 4-AA 3 mM.
[Cyclodextrin derivatives]
  DM-α-CD (mfd. by Wako Pure Chemical Industries, Ltd.)
  HP-α-CD (hydroxypropyl-α-cyclodextrin) (mfd. by Wako Pure Chemical Industries, Ltd.)
  Poly-β-DC (poly-β-cyclodextrin) (mfd. by Wako Pure Chemical Industries, Ltd.)
[Measuring conditions]

Measuring parameters were set as follows to measure cholesterol in each sample.
  Measuring method; 2 Point end [16]–[34]
  Sample amount: 3 µl
  R-1: 270 µl
  R-2: 90 µl
  Measuring wavelength: 700/600 nm
  Measuring temperature: 37° C.
  Standard substance concentration: 100 mg/dl
[Results]

Conversion (%) of each lipoprotein was obtained in the same manner as described in Example 1.

The results are shown in Table 2.

TABLE 2

| Cyclodextrin derivatives | Converson of lipoproteins (%) | | | |
|---|---|---|---|---|
| (Concentration in R-1) | LDL | HDL | VLDL | CM |
| No addition | 100 | 58 | 100 | 100 |
| DM-α-CD (0.06%) | 102 | 33 | 3 | 2 |
| HP-α-CD (0.1%) | 96 | 40 | 15 | 21 |
| DM-α-CD (0.1%) Poly-β-CD (0.01%) | 104 | 9 | 0 | 0 |

As is clear from the results shown in Table 2, when the cholesterol measurement is carried out in the presence of the special cyclodextrin derivative(s), the reaction of lipoproteins other than LDL are remarkably suppressed. Particularly when DM-α-CD and poly-β-CD are co-used, lipoproteins other than LDL hardly react. In contrast, when measured in the absence of a cyclodextrin derivative, reactions of VLDL and CM are not suppressed at all, resulting in failing to measure LDL-cholesterol specifically.

As mentioned above, when the cholesterol in lipoproteins is measured in the presence of at least one compound selected from the group consisting of DM-α-CD, poly-β-CD, the cholesterol in LDL can be measured specifically.

EXAMPLE 4

Using Hitachi 7170 type autoanalyzer (mfd. by Hitachi, Ltd.), cholesterol in various lipoproteins fractionated by ultracentrifugation was measured according to a process of the present invention for studying reactivity of cholesterol.

[Samples]
The same as Example 3.

[Reagents]
R-1: 25 mM PIPES-NaOH buffer (pH 7.2) containing
  (i) 4-AA 1.2 mM,
  (ii) CHE (mfd. by Asahi Kasei Kogyo K.K.) 1 u/ml, and
  (iii) a cyclodextrin derivative as shown in Table 3
R-2: 25 mM PIPES-NaOH buffer (pH 7.2) containing
  (i) COD (mfd. by Amano Pharmaceutical Co., Ltd.) 4 u/ml,
  (ii) POD (mfd. by Toyobo Co., Ltd.) 6 u/ml, and
  (iii) HDAOS 1.2 mM

[Cyclodextrin derivatives]
poly-β-CD (mfd. by Wako Pure Chemical Industries, Ltd.)

[Measuring conditions]
The same as Example 3.

[Results]
Conversions of individual lipoproteins were obtained in the same manner as describe in Example 3.
The results are shown in Table 3.

TABLE 3

| Cyclodextrin derivatives | Converson of lipoproteins (%) | | | |
|---|---|---|---|---|
| (Concentration in R-1) | LDL | HDL | VLDL | CM |
| No addition | 75 | 97 | 75 | 38 |
| Poly-β-CD (0.13%) | 99 | 10 | 32 | 16 |

As is clear from the results of Table 3, when the cholesterol measurement is carried out in the presence of a first reagent comprising poly-β-CD and CHE, the reaction with LDL is not influenced at all, and the reactions with lipoproteins other than LDL are remarkably suppressed, resulting in making specific measurement of LDL-cholesterol possible. In contrast, when the first reagent contains only CHE, not only the reactions with lipoproteins other than LDL, particularly the reactions with HDL and VLDL, are hardly suppressed but also the reaction with LDL is considerably suppressed, resulting in failing to measure the cholesterol in LDL specifically.

EXAMPLE 5

Using Hitachi 7170 type autoanalyzer (mfd. by Hitachi, Ltd.), LDL-cholesterol in serum was measured.

[Samples]
Eight samples were obtained from fresh human serum.

[Reagents]
(Reagent 1)
R-1: 25 mM PIPES-NaOH buffer (pH 7.2) containing
  (i) 4-AA 1.2 mM, and
  (ii) poly-β-CD 0.13%
R-2: 25 mM PIPES-NaOH buffer (pH 7.2) containing
  (i) COD (mfd. by Toyobo Co., Ltd.) 4 u/ml,
  (ii) CHE (mfd. by Amano Pharmaceutical Co., Ltd.) 4 u/ml,
  (iii) POD (mfd. by Toyobo Co., Ltd.) 6 u/ml,
  (iv) HDAOS 1.2 mM, and
  (v) Lipomin LA 0.4%

(Reagent 2)
R-1: 25 mM PIPES-NaOH buffer (pH 7.2) containing
  (i) 3-AA 1.2 mM,
  (ii) CHE (mfd. by Amano Pharmaceutical Co., Ltd.) 1 u/ml,
  (iii) poly-β-CD 0.13%, and
  (iv) Lipomin LA (a trade name of aminocarboxylic acid derivative, mfd. by Lion Corp.)
R-2: 25 mM PIPES-NaOH buffer (pH 7.2) containing
  (i) COD (mfd. by Toyobo Co., Ltd.) 4 u/ml,
  (ii) POD (mfd. by Toyobo Co., Ltd.) 6 u/ml, and
  (ii) HDAOS 1.2 mM (Reagent 3)
R-1: 25 mM PIPES-NaOH buffer (pH 7.2) containing
  (i) 4-AA 1.2 mM,
  (ii) poly-β-CD 0.13%,
  (iii) CHE (mfd. by Amano Pharmaceutical Co., Ltd.) 1 u/ml, and
  (iv) Lipomin LA 0.1%
R-2: 25 mM PIPES-NaOH buffer (pH 7.2) containing
  (i) COD (mfd. by Toyobo Co, Ltd.) 4 u/ml,
  (ii) CHE (mfd. by Amano Pharmaceutical Co., Ltd.) 4 u/ml,
  (iii) POD (mfd. by Toyobo Co., Ltd.) 6 u/ml, and
  (iv) HDAOS 1.2 mM (Reagent 4)
R-1: 25 mM PIPES-NaOH buffer (pH 7.2) containing
  (i) 4-AA 1.2 mM
  (ii) CHE (mfd. by Amano Pharmaceutical Co., Ltd.) 1 u/ml, and
  (iii) Lipomin LA 0.1%
R-2: 25 mM PIPES-NaOH buffer (pH 7.2) containing
  (i) COD (mfd. by Toyobo Co., Ltd.) 4 u/ml,
  (ii) POD (mfd. by Toyobo Co., Ltd.) 6 u/ml, and
  (iii) HDAOS 1.2 mM

[Measuring conditions]
The same as Example 3

[Results]
The results are shown in Table 4.

Reference Example 1

As to the serum sample used in Example 5, the cholesterol value in LDL was calculated by the Friedewald equation according to a conventional method.

TABLE 4

| | Example 5 | | | | Reference Example 1 |
|---|---|---|---|---|---|
| Sample No. | Reagent 1 (mg/dl) | Reagent 2 (mg/dl) | Reagent 3 (mg/dl) | Reagent 4 (mg/dl) | (mg/dl) |
| 1 | 155 | 136 | 135 | 186 | 130 |
| 2 | 118 | 86 | 87 | 141 | 81 |
| 3 | 104 | 87 | 89 | 133 | 75 |
| 4 | 132 | 104 | 106 | 157 | 101 |
| 5 | 101 | 77 | 79 | 129 | 70 |
| 6 | 155 | 136 | 137 | 192 | 130 |

TABLE 4-continued

| | Example 5 | | | | Reference |
|---|---|---|---|---|---|
| Sample No. | Reagent 1 (mg/dl) | Reagent 2 (mg/dl) | Reagent 3 (mg/dl) | Reagent 4 (mg/dl) | Example 1 (mg/dl) |
| 7 | 184 | 167 | 167 | 219 | 161 |
| 8 | 159 | 139 | 140 | 198 | 138 |
| Mean value | 138.5 | 116.5 | 117.4 | 169.4 | 110.8 |
| Coefficient of corelation with Reference Example 1 | 0.994 | 0.996 | 0.996 | 0.998 | — |
| Inclination of regression line | 1.13 | 1.04 | 1.05 | 0.995 | — |
| y Intercept of regression line | −46.4 | −9.90 | −13.41 | −57.73 | — |

As is clear from the results shown in Table 4, the LDL-cholesterol values obtained by using the reagents of the present invention containing poly-β-CD (i.e. Reagents 1 to 3) are close to the LDL-cholesterol value calculated by the conventional Friedewald equation shown in Reference Example 1 compared with that obtained by using the reagents containing no poly-β-CD (i.e. Reagent 4). In other words, the LDL-cholesterol can be measured specifically according to the present invention.

Further, when Poly-β-CD is used together with an amphoteric surfactant, and if necessary with CHE (Reagents 2 and 3), the obtained LDL-cholesterol values are closer to that obtained by calculating the Friedewalt equation than the case of using poly-β-CD alone.

EXAMPLE 6

Using Hitachi 7170 type autoanalyzer (mfd. by Hitachi, Ltd.), LDL-cholesterol in serum was measured.

[Samples]

Fifteen samples were obtained from fresh human serum.

[Reagents]

R-1: 25 mM 2-hydroxy-N-tris(hydroxymethyl)-methyl-3-aminopropanesulfonic acid (TAPSO)-NaOH buffer (pH 7.0) containing
(i) HDAOS 0.6 mM
(ii) CHE (mfd. by Amano Pharmaceutical Co., Ltd. 2 U/ml
(iii) Poly-β-CD (poly-β-cyclodextrin) 0.125% (mfd. by Wako Pure Chemical Industries, Ltd.)
(iv) a surfactant shown in Table 5 0.15%

R-2: 25 mM TAPSO-NaOH buffer (pH 7.0) containing
(i) COD (mfd. by Toyobo Co., Ltd.) 4 U/ml
(ii) POD (mfd. by Toyobo Co., Ltd.) 10 U/ml
(iii) 4-AA 6 mM

[Surfactant]

Lipomin LA (a trade name, mfd. by Kao Corp.)

EMALEX 712 (a trade name, mfd. by Nihon Emulsion Co., Ltd.), polyoxyethylene lauryl ethers EMALEX 1615 (a trade name, mfd. by Nihon Emulsion Co., Ltd.), polyoxyethylene hexyldecyl ethers EMALEX NP-20 (a trade name, mfd. by Nihon Emulsion Co., Ltd.), polyoxyethylene nonylphenyl ethers

[Measuring conditions]

The same as Example 3

[Results]

The results are shown in Table 5.

Reference Example 2

As to the serum sample used in Example 5, the cholesterol value in LDL was calculated by the Friedewald equation according to a conventional method.

TABLE 5

| | Example 6 Cholesterol value (mg/dl) | | | | |
|---|---|---|---|---|---|
| | Surfactant | | | | Reference |
| Sample No. | No addition | Lipomin LA | Emalex 712 | Emalex 1615 | Emalex NP-20 | Example 2 |
| 1 | 220.3 | 153.2 | 94.6 | 207.9 | 189.8 | 149.3 |
| 2 | 213.1 | 154.2 | 102.7 | 230.1 | 218.1 | 160.0 |
| 3 | 203.5 | 147.1 | 85.4 | 205.5 | 192.6 | 166.6 |
| 4 | 230.8 | 160.2 | 93.8 | 227.2 | 199.6 | 179.1 |
| 5 | 233.7 | 166.6 | 95.8 | 227.5 | 208.1 | 193.2 |
| 6 | 259.2 | 180.0 | 99.4 | 245.4 | 221.5 | 203.8 |
| 7 | 94.0 | 105.1 | 73.9 | 168.8 | 160.8 | 122.3 |
| 8 | 191.3 | 145.4 | 93.5 | 213.9 | 202.1 | 158.0 |
| 9 | 142.3 | 126.3 | 91.1 | 191.6 | 186.1 | 127.8 |
| 10 | 177.9 | 147.4 | 95.0 | 211.1 | 205.2 | 150.0 |
| 11 | 204.5 | 149.9 | 93.7 | 213.8 | 194.8 | 147.1 |
| 12 | 294.3 | 238.5 | 124.3 | 248.9 | 249.2 | 247.0 |
| 13 | 237.7 | 170.2 | 102.1 | 234.1 | 219.6 | 175.3 |
| 14 | 291.5 | 202.7 | 123.4 | 273.9 | 260.4 | 224.2 |
| 15 | 253.5 | 171.1 | 106.2 | 247.4 | 238.8 | 189.9 |
| Mean value | 216.5 | 161.2 | 98.3 | 223.1 | 209.8 | 172.9 |
| Correlation with Reference Example 2 | 0.914 | 0.959 | 0.848 | 0.881 | 0.878 | — |
| Inclination of regression line | 0.598 | 1.063 | 2.270 | 1.174 | 1.171 | — |
| y Intercept of regression line | 43.437 | 1.571 | −50.338 | −89.035 | −72.813 | — |

As is clear from the results shown in Table 5, the LDL-cholesterol values obtained by using the reagents of the present invention containing poly-62 -CD and Lipomin LA are close to the LDL-cholesterol value calculated by the conventional Friedewald equation shown in Reference Example 2 compared with that obtained by using the reagents containing poly-β-CD and nonionic surfactant. In other words, the LDL-cholesterol can be measured specificaly according to the present invention.

EXAMPLE 7

A typical example of the kit for measuring LDL-cholesterol in a living sample such as serum and plasma is as follows.

(1) First reagent (pH 6–8)
At least one compound selected from the group consisting of DM-α-CD, HP-α-CD and poly-β-CD,
CHE,
Coupler (or a developer)

(2) Second reagent (pH 6–8)

COD,
CHE,
POD,
Developer (or a coupler)

Using such a kit, there were obtained the same results as in Example 3.

As mentioned above, according to the present invention, the LDL-cholesterol in a living sample can be measured specifically and accurately using the special reagents of the present invention. Further, by applying the present invention, the LDL-cholesterol can directly be measured by using a general-purpose autoanalyzer, which was impossible according to prior art processes.

What is claimed is:

1. A process for measuring cholesterol in low density lipoproteins present in a living sample by optically measuring a reaction product of the living sample with a reagent, which comprises conducting the reaction of the living sample with cholesterol oxidase or cholesterol dehydrogenase in the presence of an amphoteric surfactant and at least one member selected from the group consisting of cyclodextrin and derivatives thereof.

2. The process according to claim 1, wherein the cyclodextrin derivatives is at least one compound selected from the group consisting of dimethyl-α-cyclodextrin and poly-β-cyclodextrin.

3. The process according to claim 1, wherein the cyclodextrin derivatives is poly-β-cyclodextrin.

4. The process according to claim 1, wherein the amphoteric surfactant is at least one compound selected from the group consisting of alkyl betaine derivatives, imidazolinium betaine derivatives, sulfobetaine derivatives, aminocarboxylic acid derivatives, imidazoline derivatives and amine oxide derivatives.

5. The process according to claim 1, wherein the amphoteric surfactant is at least one compound selected from the group consisting of an aminocarboxylic acid derivative, lauric acid amidopropyl betaine, a 2-alkyl-N-carboxymethyl-N-hydroxyethyl imidazolinium betaine, lauryl betaine, sodium N-lauroyl-N-methyl-β-alanine and N-octyl-N,N-dimethyl-3-ammonio-1-propanesulfonic acid.

6. The process for measuring cholesterol in low density lipoproteins present in a living sample which comprises,
treating the living sample with a first reagent comprising at least one member selected from the group consisting of cyclodextrin and derivatives thereof,
measuring an absorbance or transmittance of the resulting solution,
treating the resulting solution with a second reagent solution containing cholesterol oxidase,
measuring another absorbance or transmittance of the resulting final solution, and
providing the cholesterol amount in the living sample on the basis of the absorbance or transmittance data measured above,
wherein a coupler, a developer, peroxidase, an amphoteric surfactant and cholesterol esterase are contained in at least either the first reagent or the second reagent.

7. The process according to claim 6, wherein the concentration of cyclodextrin or derivatives thereof is 0.0001 to 10% (w/v) in the final solution.

8. The process according to claim 6, wherein the concentration of the amphoteric surfactant is 0.0001 to 10% (w/v) in the final solution.

9. The process for measuring cholesterol in low density lipoproteins present in a living sample, which comprises
treating the living sample with a first reagent comprising at least one member selected from the group consisting of cyclodextrin and derivatives thereof,
measuring an absorbance or transmittance of the resulting solution,
treating the resulting solution with a second reagent solution containing cholesterol dehydrogenase,
measuring another absorbance or transmittance of the resulting final solution, and
providing the cholesterol amount in the living sample on the basis of the absorbance or transmittance data measured above
wherein nicotinamide adenine dinucleotide (phosphate), an amphoteric surfactant and cholesterol esterase are contained in at least either the first reagent or the second reagent.

10. The process according to claim 9, wherein the concentration of cyclodextrin or derivatives thereof is 0.0001 to 10% (w/v) in the final solution.

11. The process according to claim 9, wherein the concentration of the amphoteric surfactant is 0.0001 to 10% (w/v) in the final solution.

12. A reagent composition for measuring cholesterol in low density lipoproteins, which comprises cholesterol oxidase or cholesterol dehydrogenase, an amphoteric surfactant and at least one member selected from the group consisting of cyclodextrin and derivatives thereof.

13. The reagent composition according to claim 12, wherein the cyclodextrin derivative is at least one compound selected from the group consisting of dimethyl-α-cyclodextrin and poly-β-cyclodextrin.

14. The reagent composition according to claim 12, wherein the cyclodextrin derivatives is poly-β-cyclodextrin.

15. The reagent composition according to claim 12, wherein the amphoteric surfactant is at least one compound selected from the group consisting of alkyl betaine derivatives, imidazolinium betaine derivatives, sulfobetaine derivatives, aminocarboxylic acid derivatives, imidazoline derivatives and amine oxide derivatives.

16. The reagent composition according to claim 12, wherein the amphoteric surfactant is at least one compound selected from the group consisting of an aminocarboxylic acid derivative, lauric acid amidopropyl betaine, a 2-alkyl-N-carboxymethyl-N-hydroxyethyl imidazolinium betaine, lauryl betaine, sodium N-lauroyl-N-methyl-β-alanine and N-octyl-N,N-dimethyl-3-ammonio-1-propanesulfonic acid.

17. The reagent composition according to claim 12, wherein the concentration of cyclodextrin or derivatives thereof is 0.0002 to 20% (w/v).

18. The reagent composition according to claim 12, wherein the concentration of the amphoteric surfactant is 0.0001 to 20% (w/v).

19. The reagent composition for measuring cholesterol in low density lipoproteins, which comprises
(a) a first reagent containing at least one member selected from the group consisting of cyclodextrin and derivatives thereof,
(b) a second reagent containing cholesterol oxidase, and
(c) a coupler, a developer, peroxidase, an amphoteric surfactant and cholesterol esterase being contained in at least either the first reagent or the second reagent.

20. The reagent composition according to claim 19, wherein the cyclodextrin derivative is at least one compound selected from the group consisting of dimethyl-α-cyclodextrin and poly-β-cyclodextrin.

21. The reagent composition according to claim 19, wherein the cyclodextrin derivative is poly-β-cyclodextrin.

22. The reagent composition according to claim 19, wherein the amphoteric surfactant is at least one compound selected from the group consisting of alkyl betaine derivatives, imidazolinium betaine derivatives, sulfobetaine derivatives, aminocarboxylic acid derivatives, imidazoline derivatives and amine oxide derivatives.

23. The reagent composition according to claim 19, wherein the amphoteric surfactant is at least one compound selected from the group consisting of an aminocarboxylic acid derivative, lauric acid amidopropyl betaine, a 2-alkyl-N-carboxymethyl-N-hydroxyethyl imidazolinium betaine, lauryl betaine, sodium N-lauroyl-N-methyl-β-alanine and N-octyl-N,N-dimethyl-3-ammonio-1-propanesulfonic acid.

24. The reagent composition according to claim 19, wherein the concentration of cyclodextrin or derivatives thereof is 0.0002 to 20% (w/v).

25. The reagent composition according to claim 19, wherein the concentration of the amphoteric surfactant is 0.0001 to 20% (w/v).

26. A kit for measuring cholesterol in low density lipoproteins comprising
(a) a first container containing a first reagent comprising an amphoteric surfactant, cholesterol esterase, a coupler or a developer, and at least one member selected from the group consisting of cyclodextrin and derivatives thereof, and
(b) a second container containing a second reagent comprising cholesterol oxidase, cholesterol esterase, peroxidase, and a developer or a coupler.

27. The kit according to claim 26, wherein the cyclodextrin derivative is at least one compound selected from the group consisting of dimethyl-α-cyclodextrin and poly-β-cyclodextrin.

28. The kit according to claim 26, wherein the cyclodextrin derivative is poly-β-cyclodextrin.

29. The process for measuring cholesterol in low density lipoproteins present in a living sample, which comprises
reacting the living sample with cholesterol oxidase or cholesterol dehydrogenase in the presence of at least one compound selected from the group consisting of dimethyl-α-cyclodextrin and poly-β-cyclodextrin, and
measuring the cholesterol amount optically.

30. The process for measuring cholesterol in low density lipoproteins present in a living sample, which comprises
treating the living sample with a first reagent comprising at least one member selected from the group consisting of dimethyl-α-cyclodextrin and poly-β-cyclodextrin,
measuring an absorbance or transmittance of the resulting solution,
treating the resulting solution with a second reagent solution containing cholesterol oxidase,
measuring another absorbance or transmittance of the resulting final solution, and
providing the cholesterol amount in the living sample on the basis of the absorbance or transmittance data measured above,
wherein a coupler, a developer, peroxidase, and cholesterol esterase is contained in at least either the first reagent or the second reagent.

31. The process for measuring cholesterol in low density lipoproteins present in a living sample, which comprises
treating the living sample with a first reagent comprising at least one member selected from the group consisting of dimethyl-α-cyclodextrin and poly-β-cyclodextrin,
measuring an absorbance or transmittance of the resulting solution,
treating the resulting solution with a second reagent solution containing cholesterol dehydrogenase,
measuring another absorbance or transmittance of the resulting final solution, and
providing the cholesterol amount in the living sample on the basis of the absorbance or transmittance data measured above,
wherein nicotinamide adenine dinucleotide (phosphate) and cholesterol esterase are contained in at least either the first reagent or the second reagent.

32. The reagent composition, for measuring cholesterol in low density lipoproteins comprising cholesterol oxidase or cholesterol dehydrogenase, and at least one compound selected from the group consisting of dimethyl-α-cyclodextrin, and poly-β-cyclodextrin.

33. The reagent composition for measuring cholesterol in low density lipoproteins comprising
(a) a first reagent containing at least one compound selected from the group consisting of dimethyl-α-cyclodextrin and poly-β-cyclodextrin,
(b) a second reagent containing cholesterol oxidase, and
(c) a coupler, a developer, peroxidase and cholesterol esterase being contained in at least either the first reagent or the second reagent.

34. A kit for measuring cholesterol in low density lipoproteins comprising
(a) a first container containing a first reagent comprising cholesterol esterase, a coupler or a developer, and at least one compound selected from the group consisting of dimethyl-α-cyclodextrin and poly-β-cyclodextrin, and
(b) a second container containing a second reagent comprising cholesterol oxidase, cholesterol esterase, peroxidase and a developer or a coupler.

* * * * *